US010402990B2

(12) United States Patent
Popovic et al.

(10) Patent No.: US 10,402,990 B2
(45) Date of Patent: Sep. 3, 2019

(54) MEDICAL VIEWING SYSTEM WITH A VIEWING PLANE DETERMINATION

(71) Applicant: KONINKLIJKE PHILIPS N.V., Eindhoven (NL)

(72) Inventors: Aleksandra Popovic, Boston, MA (US); John Allen Bracken, Denver, CO (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 33 days.

(21) Appl. No.: 15/127,473

(22) PCT Filed: Mar. 11, 2015

(86) PCT No.: PCT/EP2015/054996
§ 371 (c)(1),
(2) Date: Sep. 20, 2016

(87) PCT Pub. No.: WO2015/140014
PCT Pub. Date: Sep. 24, 2015

(65) Prior Publication Data
US 2017/0132796 A1 May 11, 2017

(30) Foreign Application Priority Data
Mar. 21, 2014 (EP) ..................................... 14161136

(51) Int. Cl.
*A61B 5/00* (2006.01)
*A61B 6/00* (2006.01)
(Continued)

(52) U.S. Cl.
CPC .............. *G06T 7/30* (2017.01); *A61B 5/0402* (2013.01); *A61B 5/04012* (2013.01);
(Continued)

(58) Field of Classification Search
CPC ................ A61B 6/00; A61B 5/00; G06T 7/00
(Continued)

(56) References Cited

U.S. PATENT DOCUMENTS 7,831,073 B2 11/2010 Fy et al.
8,213,693 B1 * 7/2012 Li .......................... A61B 34/20
382/128

(Continued)

FOREIGN PATENT DOCUMENTS

| JP | 2010162058 A | 7/2010 |
| WO | 2005063125 | 7/2005 |
| WO | 2007049207 A1 | 5/2007 |

OTHER PUBLICATIONS

Jain, Ameet, et al "3D TEE Registration with X-Ray Fluoroscopy for Interventional Cardiac Applications" Functional Imaging and Modeling of the Hearts, LNCS, vol. 5529, pp. 321-329, 2009.

(Continued)

*Primary Examiner* — Amir Alavi

(57) ABSTRACT

A medical viewing system (10) determines a viewing plane and provides medical images with the determined viewing plane. The medical viewing system (10) includes an X-ray image acquisition device (1), an echocardiographic image acquisition device (2) and a processing unit (3). The X-ray image acquisition device (1) is adapted to acquire an X-ray image in an X-ray imaging plane. The echocardiographic image acquisition device (2) is adapted to acquire a plurality of echocardiographic images. The processing unit (3) is adapted for a determination of an indicator in the X-ray image indicating a viewing plane for an echocardiographic image. The indicator may be an indicator line (41) in the X-ray image indicating the viewing plane perpendicular to the X-ray imaging plane. The processing unit (3) is further adapted for registering or fusing the X-ray image and the plurality of echocardiographic images together, and for then (Continued)

providing an echocardiographic image in the identified viewing plane. The identified viewing plane may be related to specific plane of a device (valve clips, plugs. . .) or of a specific anatomical structure.

14 Claims, 6 Drawing Sheets

(51) Int. Cl.
G06T 7/30 (2017.01)
G06T 19/00 (2011.01)
A61B 5/04 (2006.01)
A61B 5/0402 (2006.01)
G06F 3/048 (2013.01)
G06T 7/00 (2017.01)

(52) U.S. Cl.
CPC ............. *A61B 6/463* (2013.01); *A61B 6/467* (2013.01); *A61B 6/5247* (2013.01); *G06F 3/048* (2013.01); *G06T 7/0012* (2013.01); *G06T 19/00* (2013.01); *G06T 2207/10028* (2013.01); *G06T 2207/10116* (2013.01); *G06T 2207/30048* (2013.01)

(58) Field of Classification Search
USPC .................................. 382/128–134; 600/300
See application file for complete search history.

(56) References Cited

U.S. PATENT DOCUMENTS

| 8,942,457 | B2* | 1/2015 | Florent | G06T 11/008 |
| | | | | 128/922 |
| 9,237,929 | B2 | 1/2016 | Gerard et al. | |
| 9,687,204 | B2* | 6/2017 | Mountney | A61B 6/12 |
| 10,238,361 | B2 | 3/2019 | Gogin et al. | |
| 2012/0065729 | A1 | 3/2012 | Pintor | |
| 2013/0046172 | A1* | 2/2013 | Waitzman | A61B 5/06 |
| | | | | 600/424 |
| 2013/0259341 | A1 | 10/2013 | Matthias | |
| 2014/0072191 | A1 | 3/2014 | Liang | |

OTHER PUBLICATIONS

Hatt, Charles R. et al "Efficient Feature-Based 2D/3D Registration of Transesophageal Echocardiography to X-Ray Fluoroscopy for Cardiac Interventions", Medical Imaging 2014: Image-Guided Procedures, Robotic Interventions, and Modeling, vol. 9036, pp. 1-10.
Philips: "New Pediatric Hybrid Environment" 2008 XP-002743073.
Mountney, P. "Ultrasound and Fluoroscopic Images Fusion by Autonomous Ultrasound Probe Detection", 2011.
Gao, Gang, et al "Registration of 3D Trans-esophaeal Echocardiography to X-Ray Fluoroscopy using Image-Based Probe Tracking", Medical Image Analysis, vol. 16, No. 1, 2011 Abstract Only.

* cited by examiner

MEDICAL VIEWING SYSTEM WITH A VIEWING PLANE DETERMINATION

CROSS-REFERENCE TO PRIOR APPLICATIONS

This application is the U.S. National Phase application under 35 U.S.C. § 371 of International Application No. PCT/EP2015/054996, filed on Mar. 11, 2015, which claims the benefit of European Patent Application No. 14161136.8, filed on Mar. 21, 2014. These applications are hereby incorporated by reference herein.

FIELD OF THE INVENTION

The present invention relates to a medical viewing system with a viewing plane determination, a method for providing medical images with a viewing plane determination, a computer program element for controlling such system and a computer readable medium.

BACKGROUND OF THE INVENTION

X-ray imaging (fluoroscopy) is an important imaging modality for cardiac interventions. For providing a guidance of procedures that require more soft-tissue information, for example the treatment of structural heart disease, transesophageal echocardiography (TEE) information is employed TEE imaging, which is a form of ultrasound imaging, is able to show e.g. an interventional device and its surrounding anatomy simultaneously.

It has been proposed to complement X-ray imaging with live 3D TEE imaging. In this case, the drawback of X-ray images having poor tissue contrast is alleviated using soft tissue information from the 3D TEE images. For this purpose, the X-ray image and TEE images need to be registered. For example, an article by Jain et al., "3D TEE Registration with X-Ray Fluoroscopy for Interventionak Cardiac Applications", Functional Imaging and Modeling of the Heart, LNCS vol. 5529, pp. 321-329, Springer (Heidelberg) 2009, describes registration with the aid of an electromagnetic tracking system.

When X-ray and TEE images are thus registered, there is a need to identify a view from the TEE data that optimally complements the X-ray image information.

WO 2007/049207 A1 discloses a system and a method for generating a number of standard 2D echocardiographic views from 3D image data acquired in respect of a subject. A medical practitioner positions a 3D probe so that one visualization plane corresponds to a standard 2D view and then pre-calculated relative coordinates are used to automatically locate and generate other standard 2D views. Alternatively, a landmark extraction algorithm is used to identify specific features, from which the respective visualization planes can be located and the standard 2D views generated.

Locating an optimal viewing plane for an interventional device (valve clips, plugs . . . ) in 3D TEE images is particularly challenging and time consuming, disrupting clinical workflow and increasing the chance of miscommunication. So far, defining such viewing plane has required manipulating the 3D TEE images themselves. For example, a user interface may be provided to allow rotating and cropping (i.e. defining a cut plane) of these images. Such actions have to be carried out manually, repeating them as often as needed until an optimal plane is found. Typically, multiple rotating and cropping actions are required before an acceptable result is obtained. Often, in addition, fine adjustments of the 3D probe position and orientation will be required as well.

Finally, the appropriate viewing plane for a device can change throughout the procedure, depending on whether a device is being positioned, deployed or assessed for function. Thus, several ideal viewing planes for a device could be required over the course of a single interventional procedure. Thus, it may be required to interrupt the procedure to repeat the tedious process of finding an optimal viewing plane.

SUMMARY OF THE INVENTION

Hence, there may be a need to provide a medical viewing system which improves the process of selecting and providing a device viewing plane in ultrasound images, in particular 3D TEE images.

According to the present invention, a medical viewing system comprises an X-ray image acquisition device, an echocardiographic image acquisition device and a processing unit. The X-ray image acquisition device is adapted to acquire an X-ray image in an X-ray imaging plane, wherein the X-ray image includes an interventional device. The echocardiographic image acquisition device is adapted to acquire an echocardiographic image, preferably a 3D TEE image. The system further includes a user interface for providing, in the X-ray image, an indicator for indicating a viewing plane comprising the interventional device. The processing unit is adapted for registering or fusing the X-ray image and the echocardiographic image together, and for then selecting or providing a view of the electrocardiographic image in accordance with the identified viewing plane. The indicator may preferably be an indicator line in the X-ray image, in which case a viewing plane may be defined as comprising the indicator line and being perpendicular to the X-ray imaging plane.

The identified viewing plane is advantageously related to specific plane of an interventional device such as a valve clip or a plug.

To improve, simplify and speed up the determination of a suitable viewing plane for interventional devices in echocardiographic images, preferably 3D TEE images, during an interventional procedure, viewing plane selection of the device may be identified by initially drawing an indicator in the X-ray images. For example, an indicator line is drawn that defines a viewing plane perpendicular to the X-ray imaging plane. When the X-ray and echocardiographic images are registered (or fused) together, then a view of the echocardiographic image corresponding to a desired or optimal viewing plane for the interventional device, as identified by the user in the X-ray images, may then be automatically displayed.

The medical viewing system according to the present invention thus is configured to enable a viewing plane determination for the echocardiographic image. The invention simplifies, accelerates and improves the process of selecting a desired device viewing plane in echocardiographic images by using complementary device information that is already present in X-ray images used to guide these procedures. In particular, the inventors realized that the interventional device is generally well-recognizable in the live X-ray images. Thus, they had the insight to make use of the device information shown in the X-ray image in setting up an optimal view of the interventional device in the echocardiographic image.

Advantageously, this helps to reduce or even eliminate rotating and cropping the echocardiographic image to find the best view for the interventional device. As a result, also the number of echocardiographic probe adjustments that the echocardiographer needs to make during the procedure may be reduced.

The X-ray image acquisition device may preferably comprise a C-arm assembly, which includes a C-arm structure with an X-ray source and an X-ray detector mounted across from the X-ray source and a motorized drive for a rotational movement of the C-arm structure. The C-arm structure is provided to perform a rotational scan around an axis of rotation and around an ISO-center acquiring a number of X-ray projections at variable viewing angles. The processing unit, which is connected to the X-ray image acquisition device, is capable of controlling the motion of the C-arm structure and the acquisition of X-ray images.

The echocardiography imaging device is to be understood as an imaging device having a probe containing an ultrasound transducer at its tip, which probe may be passed into or placed onto the patient's body, for providing live ultrasound images and/or Doppler evaluation. The probe may be chosen from a variety of different probes, such as a transesophageal echocardiography (TEE) probe, which is to be inserted into the patient's esophagus, or a transthoracic echocardiography (TTE) probe, which is to be placed onto the patient's thorax. In particular, TEE provides cardiologists with real-time three-dimensional (3D) ultrasound imaging of cardiac anatomy.

The processing unit is to be understood as a computing unit having a processor, a memory and an interface for receiving user inputs and live image data from the X-ray image acquisition device and the echocardiography imaging device and for outputting data and control signals. Further, the processing unit is adapted for executing a number of algorithms for performing the above mentioned functions.

As stated above, the indicator may be an indicator line in the X-ray image, whereby the viewing plane comprises the indicator line and extends perpendicular to the X-ray imaging plane. In this case, the viewing plane is completely fixed and both cropping and rotating in order to find the TEE viewing plane may be greatly reduced or even eliminated.

However, an additional indication complementing the indicator is also possible. Then, the processing unit may be adapted for a determination of the additional indication in the echocardiographic image to determine, together with the indicator defined in the X-ray image, the viewing plane, which in this case may be non-perpendicular and oblique to the X-ray imaging plane. The additional indication is, for example, attached by a user to a landmark in the 3D TEE image, which landmark he would like to have present in the viewing plane in addition to the interventional device.

Alternatively, the indicator may be an indicator point in the X-ray image determining a projection line perpendicular to the X-ray imaging plane. The viewing plane may be selected by means of a rotation of image data about the projection line.

The imaging line may further be e.g. expanded to an imaging band in a plurality of 2D echocardiographic images or to an imaging cylinder, sphere, cuboid, prism or the like in a plurality of 3D echocardiographic images. In other words, the identified viewing plane may be expanded into a viewing volume. The processing unit may further be adapted for a rotation of the imaging line, the imaging band and/or the imaging cylinder in the plurality of echocardiographic images. These possibilities further improve the process of selecting and providing a desired device viewing plane in echocardiographic images.

In an example, the processing unit may be adapted for a determination of indicators in different X-ray images in different X-ray imaging planes. The different X-ray images in different X-ray imaging planes may be achieved by either multiple X-ray imaging projection angles from a single C-arm system or by simultaneous X-ray imaging planes from a biplane X-ray C-arm system.

In a further example, the processing unit may be adapted to provide an echocardiographic preparation image in the X-ray imaging plane presenting the defined indicator. Also this preparation image further simplifies and accelerates the determination of a suitable viewing plane for interventional devices in echocardiographic images.

In a further example, the processing unit may be adapted to present an imaging scope or field of view of the echocardiographic image acquisition device in the X-ray image. The processing unit may further be adapted to present an echocardiographic probe in the X-ray image to further improve the determination of a suitable viewing plane.

Preferably, the echocardiographic image acquisition device is a transesophageal echocardiographic (TEE) image acquisition device. It may comprise a pediatric or an adult echocardiography probe.

Preferably, the X-ray image acquisition device and the echocardiographic image acquisition device are adapted to acquire images of an interventional device relative to an anatomy in a patient. They may also acquire images of an interventional device in specific views for specific tasks or stages of a structural heart disease intervention. The determination of an indicator may also comprise a placing of a plane-determining indicator manually or automatically on the device in the X-ray image, so that a specific predefined viewing plane can be automatically found, which can be useful for specific tasks during various structural heart disease interventions. The determination of an indicator may also comprise a placing of a plane-determining indicator physically on the device itself, so that the indicator can be automatically found to identify the viewing plane for the echocardiographic image.

Preferably, the X-ray image acquisition device and the echocardiographic image acquisition device are adapted to acquire live or continuous images, and the processing unit is adapted for registering the live or continuous images with near real-time frame rates and automatically providing the echocardiographic images in the identified viewing plane.

The identified viewing plane may be related to specific plane of a device (valve clips, plugs . . . ) or of a specific anatomical structure. The medical viewing system may automatically locate a device or structure of interest in the X-ray images and automate the generation of a specific preset view in the TEE images for the device, which would be used to guide a specific task of a specific structural heart disease intervention. The medical viewing system may therefore comprise respective control buttons and/or icons that when clicked automatically place plane-determining indicators on the device or structure in the X-ray image, automatically locate a device or structure in the X-ray image and/or automatically generate an echocardiographic image in a identified or preset viewing plane. This can improve a wide range of structural heart disease interventions (i.e. mitral clip, LAA closure etc.).

The applications for the present medical viewing system are suitable to improve device viewing when using fused X-ray/TEE imaging, mainly in the field of interventional cardiology. However, this approach can also be extended to other medical applications that use combined X-ray and ultrasound imaging such as e.g. brachytherapy.

According to the present invention, also a method for providing medical images with a viewing plane determination is presented. It comprises the following steps:

acquiring an X-ray image including an interventional device, acquiring an echocardiographic image, providing an indicator in the X-ray image indicating a viewing plane comprising the interventional device, registering the X-ray image and the echocardiographic image, selecting and providing a view of the echocardiographic image in accordance with the identified viewing plane.

It shall be understood that the medical viewing system, the method for providing medical images with a viewing plane determination, the computer program element for controlling such system and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim. These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Live X-ray imaging (fluoroscopy) and live transesophageal echocardiography (TEE) imaging are used to guide interventional cardiology procedures. During these procedures, the interventional cardiologist will often want to see the orientation of a device (e.g. valve clips, plugs and prosthetic valves) in a patient relative to the anatomy surrounding the device. This will help the cardiologist to position, deploy and assess function of the device. To avoid a repeated rotation and cropping of images, along with continuous manual adjustment of a TEE probe, the medical viewing system with viewing plane determination according to the present invention simplifies, accelerates and improves the process of selecting a desired device viewing plane in echocardiographic images by using complementary device information that is already present in X-ray images used to guide these procedures. This helps to minimize the amount of echocardiographic image rotation and cropping to find the best view and to reduce the number of echocardiographic probe adjustments that the echocardiographer needs to make during the procedure.

Figure 1:
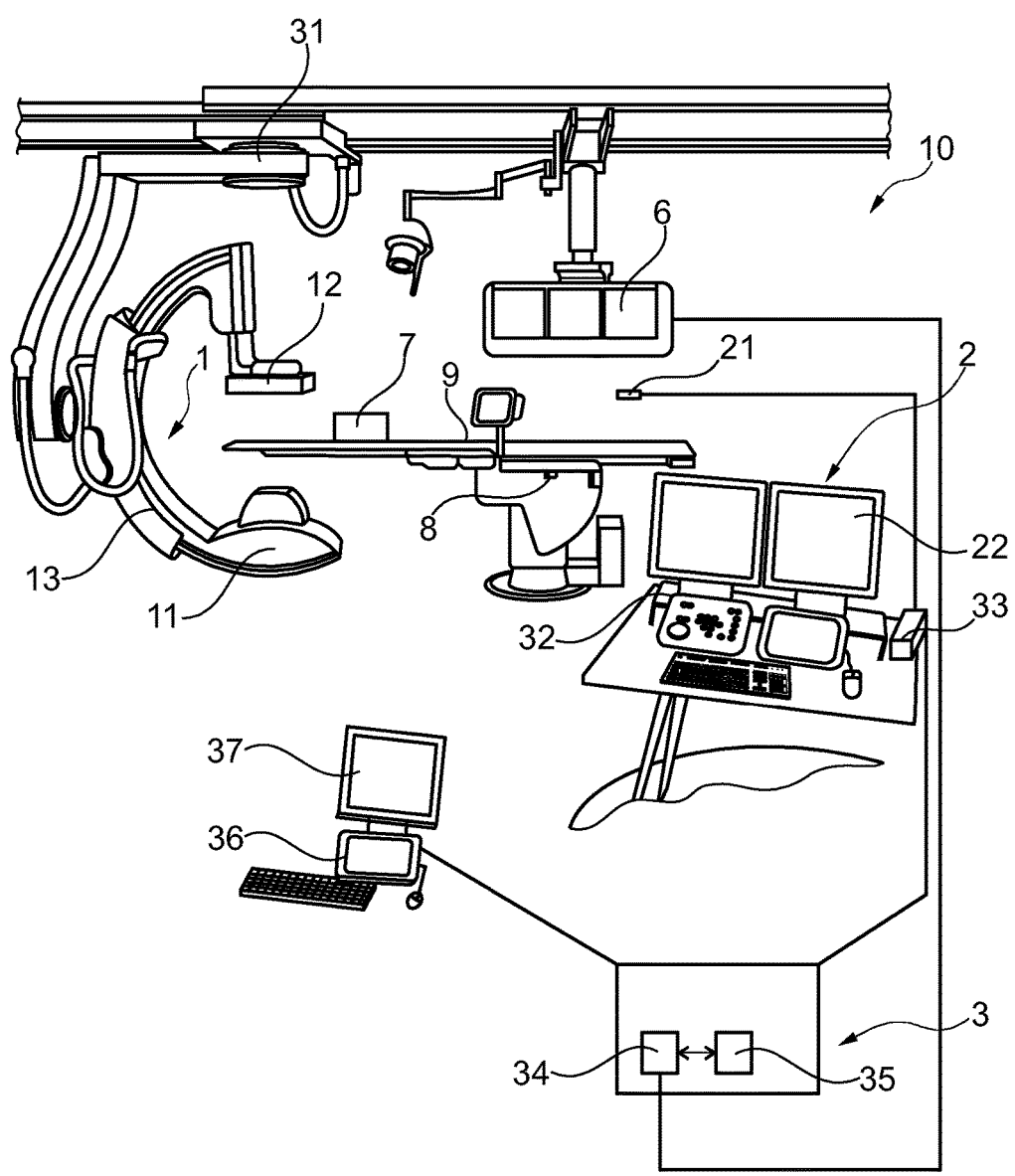
FIG. 1 is a schematic drawing of a medical system comprising an exemplary medical viewing system.

FIG. 1 is a schematic drawing of an example of a medical system. The medical system comprises an example of a medical viewing system 10 according to the present invention. The medical system further comprises a support table 9 for e.g. a patient, a control unit 8 for the support table 9, a contrast agent injector 7 and a large screen display 6 with multiple inputs.

The exemplary medical viewing system 10 according to the present invention comprises an X-ray image acquisition device 1, an echocardiographic image acquisition device 2, and a processing unit 3. The X-ray image acquisition device 1 and the echocardiographic image acquisition device 2 are connected with the processing unit 3.

The X-ray image acquisition device 1 comprises an X-ray source 11, an X-ray detector 12, and an X-ray calculation unit 31. The X-ray source 11 and the X-ray detector 12 are arranged at both ends of a C-arm 13, respectively. The X-ray source 11 and the X-ray detector 12 are connected with the X-ray calculation unit 31. The X-ray image acquisition device 1 acquires X-ray images in X-ray imaging planes. Different X-ray images may be achieved in different X-ray imaging planes by either multiple X-ray imaging projection angles from the C-arm 13 or by simultaneous X-ray imaging planes from a biplane X-ray C-arm system (not shown).

The echocardiographic image acquisition device 2 comprises an ultrasonic or TEE probe 21, an echocardiographic calculation unit 32, an echocardiography imaging device 33, and a display 22 for the echocardiography imaging device 33. The ultrasonic or TEE probe 21 is connected with the echocardiography imaging device 33 which is connected with the echocardiographic calculation unit 32.

The processing unit 3 can be one piece, but is here divided in several units arranged separately. As stated above, the processing unit 3 comprises the X-ray calculation unit 31, the echocardiographic calculation unit 32 and the echocardiography imaging device 33. The processing unit 3 further comprises an image data providing unit 34, an image data processing unit 35, a registering system 36 for registering live X-ray and live echocardiography images, and a display 37 for presenting the registered live X-ray and echocardiography images. The registered live X-ray and echocardiography images can also be presented on the large screen display 6. The image data providing unit 34 and the image data processing unit 35 are connected and receive input by the X-ray calculation unit 31 and the echocardiography imaging device 33. The image data providing unit 34 and the image data processing unit 35 are further connected and give output to the registering system 36 and the displays 37 and 6.

The processing unit 3 is used to define or defines automatically an indicator in an X-ray image taken by the X-ray image acquisition device 1 to determine a viewing plane for an echocardiographic image taken by the echocardiographic image acquisition device 2. The processing unit 3 further registers or fuses the X-ray image and the echocardiographic image together. Both steps can be controlled or monitored by a person using the registering system 36 and the display 37. Then, the processing unit 3 provides the echocardiographic image in exactly the viewing plane identified by means of the X-ray image.

Figure 2:
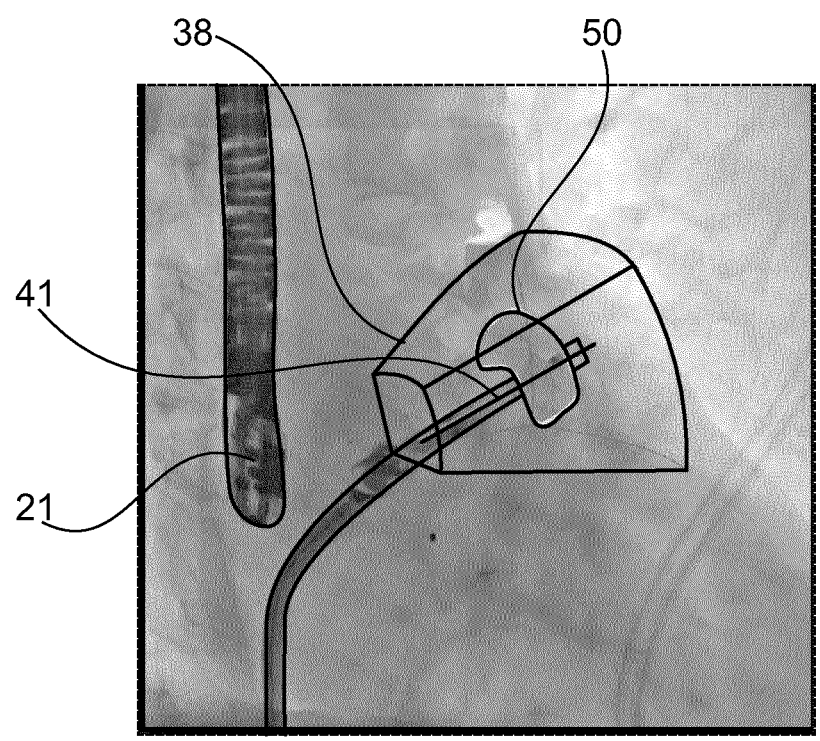
FIG. 2 is a schematic drawing of an X-ray image.

FIG. 2 is a schematic drawing of an X-ray image showing a device, in particular a plug 50, used to close a left atrial appendage (LAA) of a heart. The plug 50 has a dumbbell shape. The X-ray image also shows the TEE probe 21. As overlay, an indicator line 41 is drawn through the plug 50 to cut through the plug 50 at the desired orientation. The indicator line 41 determines a viewing plane for an echocardiographic image perpendicular to the shown X-ray imaging plane.

A further overlay shows a cone presenting an imaging field or scope 38 of the echocardiographic image acquisition device 3 in the X-ray image, which further improves the process of selecting a viewing plane for the echocardiographic images.

Figure 3:
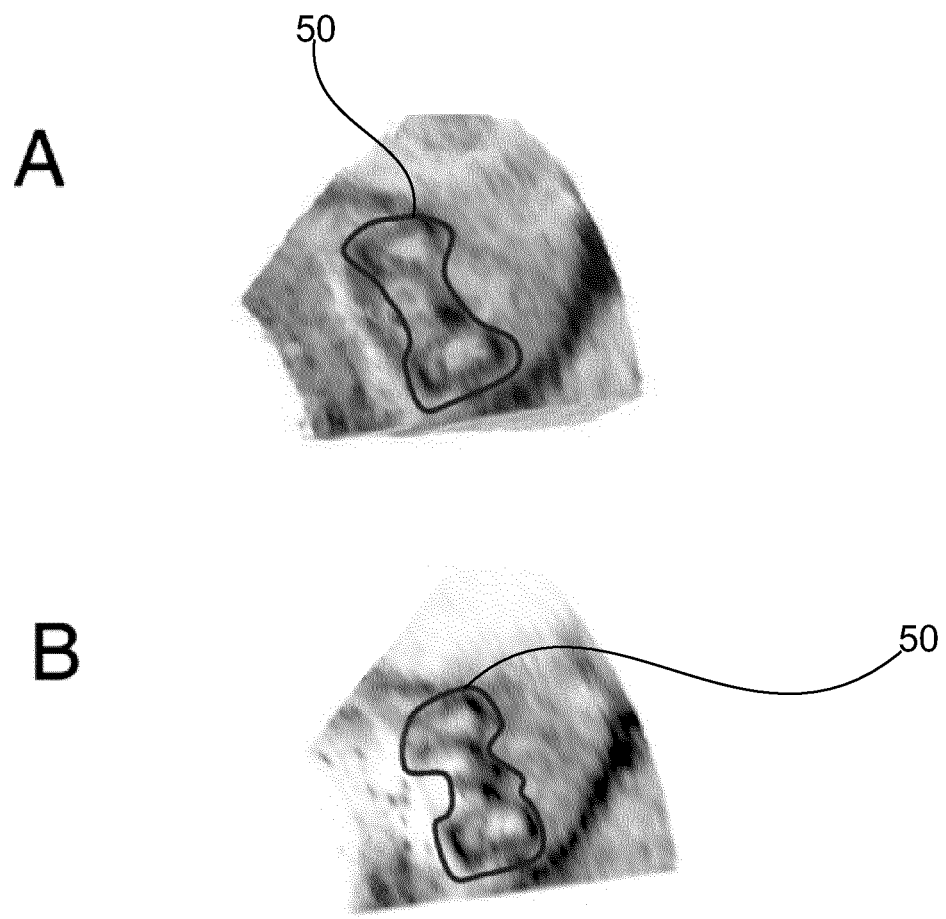
FIG. 3A is a schematic drawing of a 3D TEE image.
FIG. 3B is a schematic drawing of a 2D TEE image.

FIG. 3A is a schematic drawing of a 3D TEE image and FIG. 3B is a schematic drawing of a 2D TEE image, both showing a cross-section of the plug 50 used to close the left atrial appendage. The TEE images are approximately in the viewing plane identified by means of the X-ray image as explained to FIG. 1. The TEE images are perpendicular to the X-ray imaging plane. The TEE images are automatically generated in the viewing plane defined by the indicator line 41.

Figure 4:
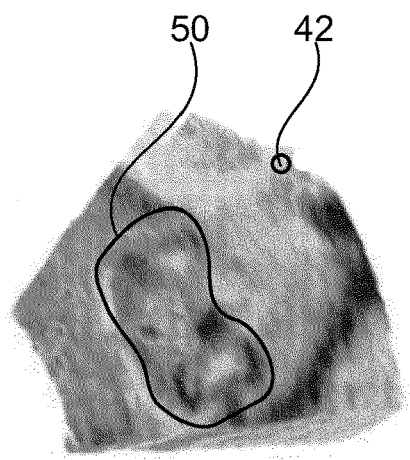
FIG. 4 is a schematic drawing of a further 3D TEE image.

FIG. 4 is a schematic drawing of a further 3D TEE image showing a cross-section of the plug 50. An additional indication 42 is defined in the TEE image. The additional indication 42 determines, together with an indicator defined in an X-ray image, another viewing plane, which is non-perpendicular or oblique to the X-ray imaging plane.

In other words, an oblique viewing plane is identified by, first, drawing an indicator line 41 in an X-ray image as shown e.g. in FIG. 2. Second, an additional indication 42 is placed in a TEE image that is perpendicular to the X-ray image plane, to provide an extra point needed to define an oblique viewing plane as shown e.g. in FIG. 4. For example, the additional indication 42 is placed on a landmark visible in the TEE image.

It is also possible to generate a viewing plane from a single indicator point placed on a device, such as the plug 50 or a catheter tip, in the X-ray image. This point projects from the 2D X-ray image onto the 3D TEE volume as a projection line since the 2D X-ray image does not have depth information. This projection line is also perpendicular to the X-ray image. A volume of interest can then be cropped out of the 3D TEE image centered on the line. The size and shape of the volume can be selected by the user to focus in on the device. In addition, an alternative 2D TEE viewing plane of the device and its surrounding region of interest can be generated by assigning a thickness to that line and extracting the data encompassed within the line from the 3D TEE image volume into a 2D TEE image band or viewing plane. To generate a 2D TEE image band or viewing plane at a specific device orientation, the 3D TEE image can be rotated around the projection line first to find a desired viewing plane, before changing the thickness of the line which defines the thickness of the 2D TEE image band.

In other words, the indicator may also be an indicator point in the X-ray image determining a projection line in an echocardiographic image perpendicular to the X-ray image. In this case, a user may still need to rotate the 3D TEE image about the projection line in order to find the optimal viewing plane, however any cropping actions in the TEE image are eliminated.

Figure 5:
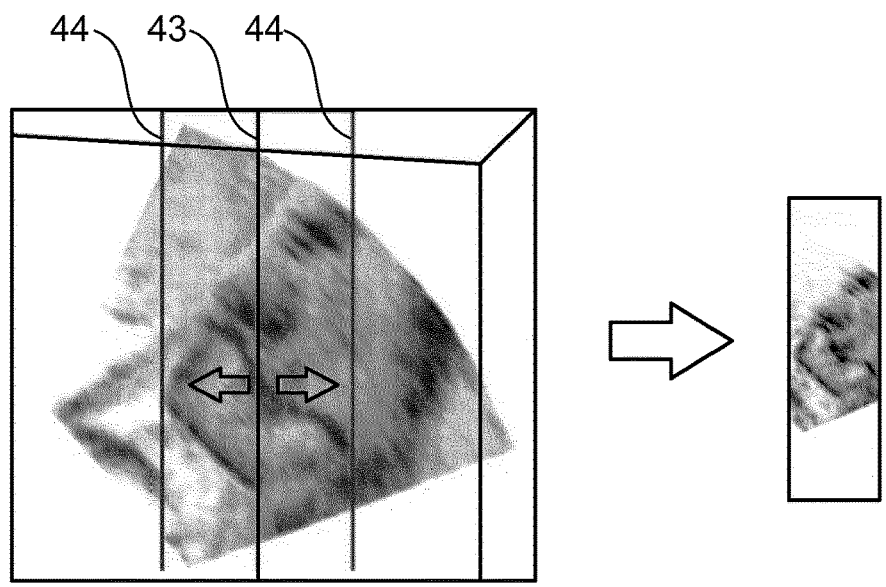
FIG. 5 is a schematic drawing of a further 2D TEE image.

FIG. 5 is a schematic drawing of such 2D TEE image showing imaging projection line 43 which was identified by an indicator point in an X-ray image. The imaging line 43 can be expanded arbitrarily, as shown in FIG. 5 by arrows and expansion lines 44, to determine a viewing plane and to form an imaging band. An imaging line 43 of a 3D TEE image can also be converted into an imaging line of a 2D TEE image, or can be used to narrow 2D TEE viewing plane.

The imaging line 43 can also be arbitrarily rotated and then expanded to an imaging band. The imaging line 43 can also be expanded into a viewing volume to form an imaging cylinder (not shown).

A single point of interest on a device, such as the plug 50 or a catheter tip, can be localized in three dimensions by positioning an indicator on two different X-ray projection images of the point of interest. Different X-ray images may be achieved in different X-ray imaging planes by either multiple X-ray imaging projection angles from the C-arm 13 or by simultaneous X-ray imaging planes from a biplane X-ray C-arm system. The point of interest can then be automatically correctly positioned in a 3D TEE image volume after the X-ray and TEE images are registered. Afterwards, an additional image cropping of the device of interest can be done, centered on that point at a volume or plane size and shape selected by the user.

Figure 6:
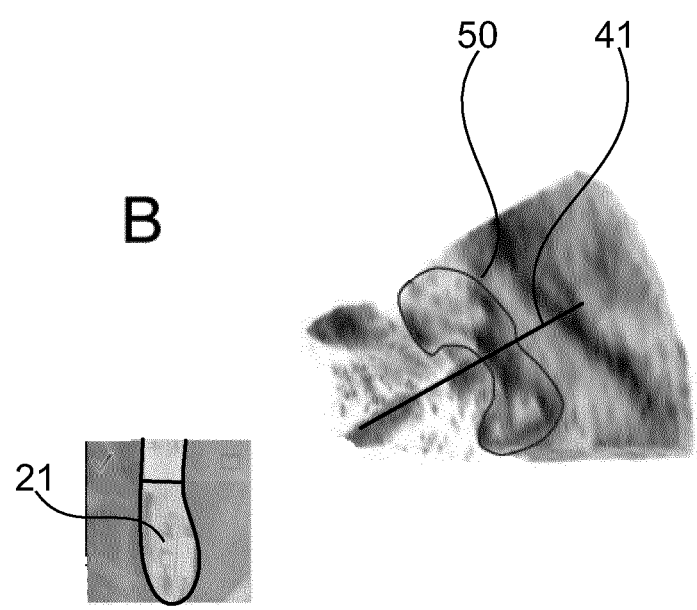
FIG. 6 shows a schematic drawing of a 3D echocardiographic preparation image.

FIG. 6 is a schematic drawing of a 3D echocardiographic preparation image showing a cross-section of the plug 50 and an overlay of the indicator line 41 similar to the X-ray image of FIG. 2. The 3D TEE preparation image is oriented at the same projection angle as the X-ray image of FIG. 2. The indicator line 41 is superimposed over the 3D TEE preparation image oriented at the same viewing projection as the X-ray image of FIG. 2. This kind of 3D TEE preparation image can provide complimentary information to help further define and position the desired viewing plane. For the same purpose, in the bottom left corner of FIG. 6, a model of the TEE probe 21 is registered to an X-ray image of the TEE probe 21.

Figure 7:
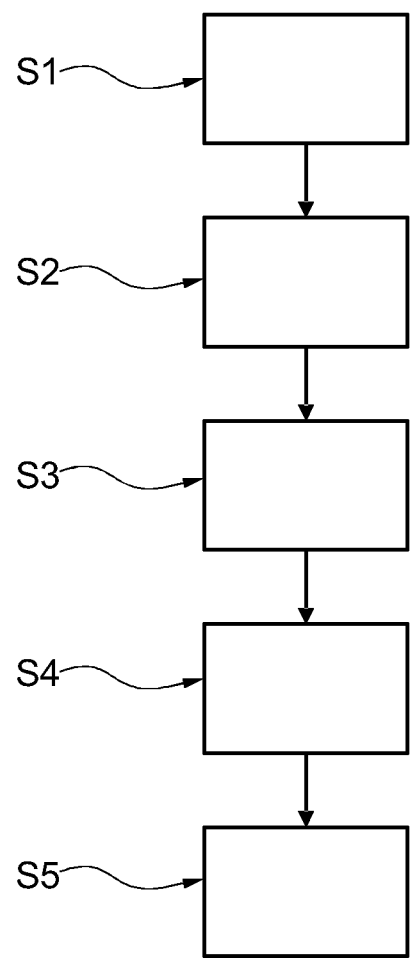
FIG. 7 shows basic steps of an example of a method for providing medical images with a viewing plane determination.

FIG. 7 shows basic steps of an example of a method for providing medical images with a viewing plane determination. It comprises the following steps, not necessarily in this order:

In step S1, acquiring an X-ray image, in step S2, acquiring a plurality of echocardiographic images, in step S3, determining an indicator in the X-ray image indicating a viewing plane for an echocardiographic image, in step S4, registering the X-ray image and the plurality of echocardiographic images, and in step S5, selecting and providing one of a plurality of echocardiographic images in the identified viewing plane.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical viewing system comprising:
an X-ray image acquisition device adapted to acquire an X-ray image in an X-ray imaging plane, the X-ray image including an interventional device;
an echocardiographic image acquisition device adapted to acquire an echocardiographic image;
a processing unit; and
a user interface for providing, in the X-ray image, an indicator for indicating a viewing plane comprising the interventional device;
wherein the processing unit is adapted to register the X-ray image and the echocardiographic image, to provide a view of the echocardiographic image in accordance with the indicated viewing plane, and to determine an additional indication in the echocardiographic image to define the viewing plane together with the indicator in the X-ray image, the defined viewing plane being non-perpendicular to the X-ray imaging plane.

2. The medical viewing system according to claim 1, wherein the indicator is an indicator point in the X-ray image defining a projection line extending through the indicator point perpendicular to the X-ray imaging plane,
wherein the user interface is further adapted to allow a rotation of the echocardiographic image about the projection line.

3. The medical viewing system according to claim 1, wherein the processing unit is further adapted to expand the identified viewing plane into a viewing volume.

4. The medical viewing system according to claim 1, wherein the processing unit is further adapted for a determination of indicators in different X-ray images in different X-ray imaging planes.

5. The medical viewing system according to claim 1, wherein the determination of the indicator is controlled by a user and/or the processing unit.

6. The medical viewing system according to claim 5, wherein the processing unit is further adapted to provide an echocardiographic preparation image in the X-ray imaging plane presenting the defined indicator.

7. The medical viewing system according to claim 6, wherein the processing unit is further adapted to present an imaging scope of the echocardiographic image acquisition device in the X-ray image.

8. The medical viewing system according to claim 1, wherein the echocardiographic image acquisition device is a 3D trans-esophageal echocardiographic (TEE) image acquisition device.

9. A medical viewing system comprising:
an X-ray image acquisition device configured to acquire an X-ray image in an X-ray imaging plane, the X-ray image including an interventional device;
an echocardiographic image acquisition device configured to acquire an echocardiographic image;
wherein the X-ray image acquisition device and the echocardiographic image acquisition device are configured to acquire live images;
a user interface configured to provide, in the X-ray image, an indicator for indicating a viewing plane comprising the interventional device;
at least one computer processor configured to register the live X-ray and echocardiographic images with near real-time frame rates and automatically provide the echocardiographic images in the identified viewing plane.

10. A method for providing medical images with a viewing plane determination, the method comprising the steps of:
acquiring live X-ray images including an interventional device,
acquiring live echocardiographic images,
providing an indicator in one of the X-ray images indicating a viewing plane comprising the interventional device,
registering the live X-ray images and the live echocardiographic images with near real-time frame rates, and
selecting and providing the echocardiographic images in the identified viewing plane.

11. A computer program element for controlling a medical imaging system, which, when being executed by one or more processors, is adapted to perform the method steps of claim 10.

12. A non-transitory computer-readable medium having computer software stored thereon, which computer software, when executed on a control processor of a medical imaging system, controls the medical imaging system to perform the method according to claim 10.

13. A medical viewing system, comprising:
- an X-ray fluoroscope configured to acquire X-ray images in an X-ray imaging plane, the X-ray images including anatomy of a patient and an interventional device;
- an echocardiographic image acquisition device configured to acquire echocardiographic images;
- a user interface configured to indicate a viewing plan in the X-ray images which viewing plane views the interventional device and at least a portion of the patient anatomy;
- one or more computer processors configured to:
    - determine an indication in the echocardiographic images of the viewing plane with the viewing plane indicated in the X-ray images, the viewing plane indicated in the echocardiographic images being non-perpendicular to the X-ray imaging plane,
    - register the X-ray images and the echocardiographic images, and
    - provide a view of the echocardiographic image in the indicated viewing plane.

14. The medical viewing system according to claim 1, wherein the indicator is an indicator line in the X-ray image and the viewing plane is selected perpendicular to the X-ray imaging plane.

\* \* \* \* \*